United States Patent
Hofmann et al.

(10) Patent No.: US 10,080,538 B2
(45) Date of Patent: Sep. 25, 2018

(54) METHOD FOR THE PROVISION OF QUANTITATIVE CT IMAGE DATA ACQUIRED FROM A SCANNING FIELD VIA A DUAL-SOURCE CT DEVICE

(71) Applicant: Siemens Healthcare GmbH, Erlangen (DE)

(72) Inventors: Christian Hofmann, Erlangen (DE); Nora Hünemohr, Stuttgart (DE); Rainer Raupach, Heroldsbach (DE); André Ritter, Buckenhof (DE)

(73) Assignee: SIEMENS Healthcare GmbH, Erlangen (DE)

( * ) Notice: Subject to any disclaimer, the term of this patent is extended or adjusted under 35 U.S.C. 154(b) by 0 days.

(21) Appl. No.: 15/807,740

(22) Filed: Nov. 9, 2017

(65) Prior Publication Data

US 2018/0146945 A1  May 31, 2018

(30) Foreign Application Priority Data

Nov. 30, 2016  (DE) .................. 10 2016 223 831

(51) Int. Cl.
*A61B 6/00* (2006.01)
*A61B 6/03* (2006.01)

(52) U.S. Cl.
CPC ............ *A61B 6/5235* (2013.01); *A61B 6/032* (2013.01); *A61B 6/4014* (2013.01)

(58) Field of Classification Search
CPC ..... A61B 6/032; A61B 6/5235; A61B 6/4014; A61B 6/482; A61B 6/5205; G06T 11/008; G06T 2211/40; G06T 2211/408
See application file for complete search history.

(56) References Cited

U.S. PATENT DOCUMENTS 8,588,363 B2  11/2013  Flohr
8,897,530 B2  11/2014  Flohr
(Continued)

FOREIGN PATENT DOCUMENTS

DE  102015206363 B3  8/2016

OTHER PUBLICATIONS

Williamson. Jeffrey F. et al.: "On two-parameter models of photon cross sections: Application to dual-energy CT imaging", in: Med. Phys.. vol. 33, No. 11, Nov. 2006, pp. 4115-4129, DOI:10.1118/1.2349688.
(Continued)

*Primary Examiner* — Glen Kao
(74) *Attorney, Agent, or Firm* — Harness, Dickey & Pierce, P.L.C.

(57) ABSTRACT

A method is for provisioning quantitative CT image data acquired from a scanning field via a dual-source CT device the dual-source CT device including a first radiation source-detector system with a first capture region and a second radiation source-detector system with a second capture region. The method includes dividing the scanning field into a first subregion, representing at least a part of the intersection of the first region and the second capture region, and a second subregion, disjoint from the second region; acquiring first CT scan data from the first subregion and second CT scan data from the second subregion; reconstructing first quantitative CT image data from the first CT scan data and second quantitative CT image data from the second CT scan data; combining the first quantitative CT image data and the second quantitative CT image data to quantitative CT image data; and provisioning the quantitative CT image data.

26 Claims, 5 Drawing Sheets

(56) References Cited

U.S. PATENT DOCUMENTS

2010/0215144 A1* 8/2010 Basu .................. G01V 5/005
 378/20
2012/0121062 A1* 5/2012 Sowards-Emmerd ......................
 G06T 11/006
 378/4
2016/0296183 A1 10/2016 Flohr

OTHER PUBLICATIONS

Alvarez. Robert E. et al.: Energy-selective Reconstructions in X-ray Computerized Tomography, Phys. Med. Biol., 1976, vol. 21, No. 5, pp. 733-744.
German Office Action #102016223831.0 dated May 23, 2017 and English translation thereof.
Decision to Grant a Patent #102016223831.01 dated Jul. 28, 2017.

* cited by examiner

METHOD FOR THE PROVISION OF QUANTITATIVE CT IMAGE DATA ACQUIRED FROM A SCANNING FIELD VIA A DUAL-SOURCE CT DEVICE

PRIORITY STATEMENT

The present application hereby claims priority under 35 U.S.C. § 119 to German patent application number DE 102016223831.0 filed Nov. 30, 2016, the entire contents of which are hereby incorporated herein by reference.

FIELD

At least one embodiment of the application generally relates to a method for the provision of quantitative CT image data acquired from a scanning field via a dual-source CT device, a computer unit for a dual-source CT device, a dual-source CT device and/or a computer program product.

BACKGROUND

The spectrally resolved CT imaging (CT imaging) of a patient enables the creation of quantitative CT image data (CT image data). Spectrally resolved CT imaging is possible, for example, by way of known dual-energy processes or with the use of energy-sensitive detectors. The quantitative CT image data can comprise information relating to a spatially resolved distribution of a material coefficient, for example, an electron density and/or a mass density and/or an effective atomic number distribution and/or a stopping power and/or a linear attenuation coefficient at a particular photon energy or for a particular photon energy spectrum, in a body of the patient. In place of a patient, the quantitative CT image data can also be acquired from any desired examination object, for example, an article or a test subject.

Particularly advantageously, dual-source CT devices are suitable for spectrally resolved CT imaging, since these can simultaneously acquire the CT scan data (CT scan data) for different energy spectra. From U.S. Pat. No. 8,588,363 B2, there is known an example dual-source CT device. From U.S. Pat. No. 8,897,530 B2, there is known a dual-source CT device by which a proportion of necrotic tissue can be determined.

In particular, where dual-source CT devices (dual-source CT devices) are used which comprise a first radiation source-detector system and a second radiator source-detector system wherein the first radiation source-detector system is operated with a different energy spectrum from that of the second radiation source-detector system, a scanning region in which spectrally resolved information is present can be smaller than a maximum possible scanning field of the dual-source CT device. A reason for this can be, in particular, that the first radiation source-detector system has a larger fan-beam arc and thus a greater capture region than the second radiation source-detector system. The spectrally resolved information then lies, in particular, only in the circular subregion of the scanning field of the dual-source CT device which, on rotation of both radiation source-detector systems is jointly covered. The first radiation source-detector system with the larger fan-beam arc can, however, typically cover the whole scanning field of the dual-source CT device, wherein the whole scanning field is larger than the subregion of the scanning field in which the spectrally resolved information is present. In the outer subregion of the scanning field which is then additionally present, with conventional reconstruction methods there is initially no spectrally resolved information, so that a calculation of the quantitative CT image data in this outer subregion is not possible with conventional spectral methods.

SUMMARY

The inventors have recognized, with conventional methods, that it is therefore only possible in the outer subregion of the scanning field in which no spectrally resolved information is present, to image exclusively the usual reconstructed CT image data which typically comprises no quantitative information regarding material coefficients. The typical reconstructed CT image data is herein based on the CT scan data acquired via the first radiation source-detector system with the larger fan-beam arc. Thus, in the outer subregion of the scanning field, although an image can be represented so that, for example, an anatomy of the patient can be displayed, a quantitative evaluation of the material coefficients in the inner subregion of the scanning field is however not possible. Thus, the spatially resolved distribution of the material coefficient is not present in the whole scanning field of the dual-source CT device.

At least one embodiment of the invention enables an improved possibility for the reconstruction and for the provision of quantitative CT image data from a scanning field. Advantageous embodiments are disclosed in the claims.

At least one embodiment of the inventive method for the provision of quantitative CT image data acquired from a scanning field via a dual-source CT device, the dual-source CT device comprising a first radiation source-detector system with a first capture region and a second radiation source-detector system with a second capture region, the first radiation source-detector system being operated with a different energy spectrum from that of the second radiation source-detector system, comprising:

division of the scanning field in a first scanning field subregion which represents at least a part of the intersection of the first capture region and the second capture region, and a second scanning field subregion which is disjoint from the second capture region, acquisition of first CT scan data from the first scanning field subregion via the dual-source CT device and acquisition of second CT scan data from the second scanning field subregion via the dual-source CT device, reconstruction of first quantitative CT image data from the first CT scan data using a first reconstruction method and reconstruction of second quantitative CT image data from the second CT scan data using a second reconstruction method which is configured differently from the first reconstruction method, combining the first quantitative CT image data and the second quantitative CT image data to quantitative CT image data, and provision of the quantitative CT image data.

At least one embodiment of the inventive solution includes a computation module, the computer unit being configured to carry out at least one embodiment of the inventive method. In this way, the computer unit according to at least one embodiment of the invention can carry out a method for the provision of quantitative CT image data acquired via a dual-source CT device from a scanning field.

For this purpose, in at least one embodiment, the computer unit comprises, in particular, a division unit for division of the scanning field into a first scanning field subregion which represents at least a part of the intersection of the first capture region and the second capture region, and a second scanning field subregion which is disjoint from the second capture region. The computer unit further comprises, in particular, an acquisition unit for the acquisition of first CT data that has been acquired from the first scanning field subregion via the dual-source CT device, and for acquisition of second CT data that has been acquired from the second scanning field subregion via the dual-source CT device. The computer unit also comprises, in particular, a reconstruction unit for reconstructing first quantitative CT image data from the first CT data using a first reconstruction method and reconstruction of second quantitative CT image data from the second CT scan data using a second reconstruction method which is configured differently from the first reconstruction method. The computer unit comprises, in particular, a combination unit for combining the first quantitative CT image data and the second quantitative CT image data to quantitative CT image data and a provision unit for providing the quantitative CT image data.

The computer unit can be configured to transmit control signals to the dual-source CT device and/or to receive and/or process control signals in order to carry out at least one embodiment of an inventive method. The computer unit can be integrated in the dual-source CT device. The computer unit can also be installed separately from the dual-source CT device. The computer unit can be connected to the dual-source CT device.

In this case, the CT data is configured, in particular, as CT scan data. The acquisition of the CT scan data can comprise, in this case, an acquisition of the CT scan data via a capture unit of the dual-source CT device. The CT scan data can then be transferred to the computer unit for further processing. The computer unit can then acquire the CT scan data via the acquisition unit.

The computer program product according to at least one embodiment of the invention is directly loadable into a memory store of a programmable computer unit and has program code segments in order to carry out at least one embodiment of an inventive method when the computer program product is executed in the computer unit. The computer program product can be a computer program or can comprise a computer program. In this way, the method according to at least one embodiment of the invention can be carried out rapidly, exactly reproducibly and robustly.

In at least one embodiment of the invention, the computer program product is configured such that it can carry out the method steps according to at least one embodiment of the invention via the computer unit. The computer unit must have the respective pre-conditions such as, for example, a suitable working memory store, a suitable graphics card or a suitable logic unit so that the respective method steps can be carried out efficiently.

In at least one embodiment of the invention, the computer program product is stored, for example, on a computer-readable medium or is deposited on a network or server from where it can be loaded into the processor of a local computer unit which processor can be directly connected to the dual-source CT device or configured as part of the dual-source CT device.

A non-transitory memory store of a programmable computer unit, including program code segments to carry out the method of an embodiment of the invention when the program code segments are executed in the computer unit.

Furthermore, control information of the computer program product can be stored on an electronically readable data storage medium. The items of control information of the electronically readable data storage medium can be configured such that they carry out at least one embodiment of an inventive method when the data storage medium is used in a computer unit. Thus, the computer program product can also constitute the electronically readable data storage medium.

A non-transitory computer readable medium, storing program code segments to carry out the method of an embodiment of the invention when the program code segments are executed via a processor.

Examples of electronically readable data storage media are a DVD, a magnetic tape, a hard disk drive or a USB stick, on which electronically readable control information, in particular software (see above) is stored. If this control information (software) is read from the data storage medium and stored in a computer unit of the CT device, all the embodiments according to at least one embodiment of the invention of the above-described methods can be carried out. At least one embodiment of the invention can therefore also proceed from the aforementioned computer-readable medium and/or the aforementioned electronically readable data storage medium.

The advantages of the computer unit according to at least one embodiment of the invention, of the dual-source CT device according to the invention and of the computer program product according to at least one embodiment of the invention substantially correspond to the advantages of the inventive method, as described in detail above. Features, advantages or alternative embodiments mentioned herein are also transferable similarly to the other claimed subject matter and vice versa. In other words, the product claims can also be further developed with the features disclosed or claimed in conjunction with a method. The corresponding functional features of the method are herein configured via suitable product modules as contained herein, in particular, hardware modules.

BRIEF DESCRIPTION OF THE DRAWINGS

The invention will now be described and explained in greater detail making reference to the example embodiments illustrated in the drawings.

In the drawings.

DETAILED DESCRIPTION OF THE EXAMPLE EMBODIMENTS

Figure 1:
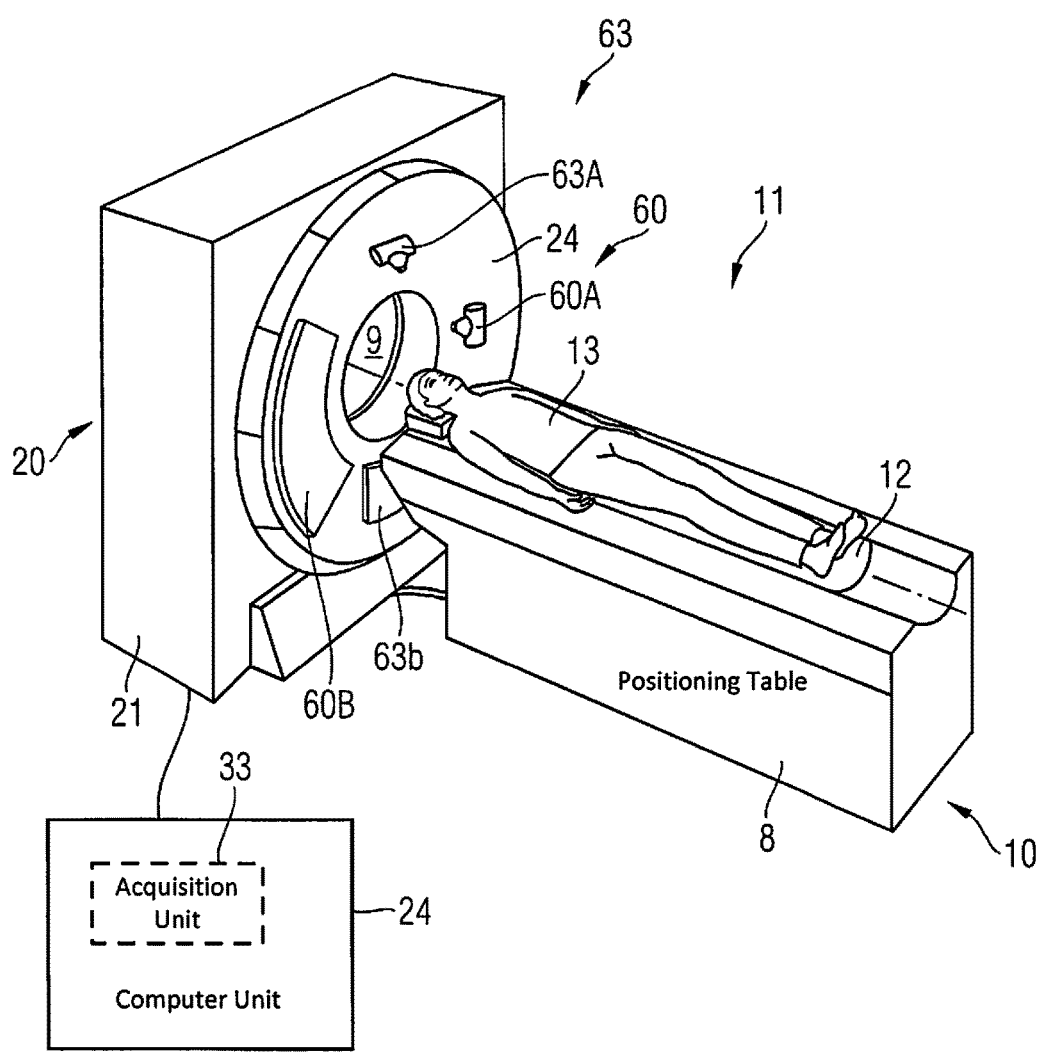
FIG. 1 shows a dual-source CT device according to the invention and a computer unit according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive method for the provision of quantitative CT image data acquired from a scanning field via a dual-source CT device, the dual-source CT device comprising a first radiation source-detector system with a first capture region and a second radiation source-detector system with a second capture region, the first radiation source-detector system being operated with a different energy spectrum from that of the second radiation source-detector system, comprising:

division of the scanning field in a first scanning field subregion which represents at least a part of the intersection of the first capture region and the second capture region, and a second scanning field subregion which is disjoint from the second capture region, acquisition of first CT scan data from the first scanning field subregion via the dual-source CT device and acquisition of second CT scan data from the second scanning field subregion via the dual-source CT device, reconstruction of first quantitative CT image data from the first CT scan data using a first reconstruction method and reconstruction of second quantitative CT image data from the second CT scan data using a second reconstruction method which is configured differently from the first reconstruction method, combining the first quantitative CT image data and the second quantitative CT image data to quantitative CT image data, and provision of the quantitative CT image data.

The dual-source CT device thus uses, in particular, a dual-energy process, since the first radiation source-detector system is operated with a different energy spectrum from that of the second radiation source-detector system. The first CT scan data from the first scanning field subregion is therefore captured, in particular, via both radiation source-detector systems. Accordingly, the first CT scan data is available in two different energy spectra, specifically a first energy spectrum at which the first radiation source-detector system is operated and a second energy spectrum at which the second radiation source-detector system is operated. The two energy spectra herein have, in particular, different maximum energies. The two radiation sources are thus typically operated at different tube voltages or acceleration voltages. It is also conceivable that the different energy spectra are obtained with different filtration of the energies.

The CT scan data is, in particular, raw data or projection data. The projection data typically comprises projection data points with, respectively, at least one projection data point value, the at least one projection point value being a measure for an attenuation of a radiation, the attenuation of the radiation relating to a radiation path attributable or attributed to each projection data point. The radiation path can extend, in particular, from a radiation source to a detector element and/or to a group of detector elements of a radiation source-detector system. In particular, a radiation path can be defined by an arrangement of the radiation source and the detector element and/or by an arrangement of the radiation source and the group of detector elements relative to a scanning field and/or relative to a region of a patient. In particular, a portion of the radiation path can extend through an examination region and/or through a region of a patient. The CT scan data is typically not directly available to a competent person for diagnosis.

Rather, making use of the CT scan data, CT image data is reconstructed which can be made available, for example, on a display unit for a competent person to make a diagnosis. The CT image data typically comprises image points with, respectively, at least one image point value, the at least one image point value being a measure for an attenuation of a radiation, the attenuation of the radiation relating to a volume element attributable or attributed to the image point. The volume element can be located, in particular, in an examination region and/or in a region of a patient. Accordingly, the CT scan data is typically placed in a projection data space and the CT image data is typically placed in an image data space. In particular, the CT image data can be reconstructed on the basis of the CT scan data via a filtered back projection (FBP).

Quantitative CT image data differs, in particular, from usual CT image data in that not only is a conventional Hounsfield unit (HU) value assigned to the image points, but a quantitative material coefficient. In this way, the quantitative CT image data can comprise, in particular, a spatially resolved distribution of the quantitative material coefficients in a body of the patient from which the CT scan data has been acquired. Possible quantitative material coefficients are: an electron density and/or a mass density and/or an effective atomic number and/or a stopping power and/or a linear attenuation coefficient at a particular photon energy or for a particular photon energy spectrum. Naturally, other quantitative material coefficients deemed useful by a person skilled in the art could also be reconstructed from the CT scan data. The quantitative material coefficient can thus advantageously characterize a physical property of the substance, for example of the tissue that is present in the volume element imaged. The quantitative material coefficient can thus provide information concerning absolute physical variables which are provided with a physical unit.

The provision of the quantitative CT image data can comprise a display of the quantitative CT image data and/or a storage of the quantitative CT image data in a database. The quantitative CT image data can alternatively or additionally be transferred to a further processing unit which can carry out a further processing of the quantitative CT image data. It is also conceivable that the quantitative CT image data is provided for planning an irradiation of the patient from whom the CT scan data has been acquired.

In at least one embodiment of the present case, it is assumed that the first radiation source-detector system has a larger fan-beam arc than the second radiation source-detector system. Thus, the first capture region of the first radiation source-detector system is larger than the second capture region of the second radiation source-detector system. The capture region of a radiation source-detector system is herein, in particular, that region from which the radiation source-detector system can acquire complete CT scan data such that from the complete CT scan data, CT image data can be reconstructed by way of a standard reconstruction technique, for example, a filtered back projection. The complete CT scan data can herein be acquired via the radiation source-detector system on a rotation of the radiation source-detector system through 180 degrees plus the respective fan-beam arcs for a typical fan-beam geometry about the respective capture regions. Due to the rotation of the radiation source-detector system about the capture region during acquisition of the CT scan data in a plane, the capture region of a radiation source-detector system is typically configured approximately circular. The second capture region herein represents, in particular, a subregion of the first capture region. Thus, the first capture region and the second capture region are arranged concentrically in one plane, the second capture region in the plane having, in particular, a smaller radius than the first capture region.

The scanning field, also known as the field of view (FOV) represents, in particular, a volume which is imaged in the quantitative CT image data. The scanning field is typically defined by a user, for example, on a scout view scan. Naturally, the scanning field can also be defined, alternatively or additionally automatically, for example, on the basis of a selected protocol. The scanning field herein represents, in particular, the whole region from which the dual-source CT device can acquire CT scan data. Herein, the scanning field is, in particular, larger than the second capture region of the second radiation source-detector system. At the same time, the scanning field is, in particular not larger than the first capture region of the first radiation source-detector system.

Spectrally resolved CT scan data is present, in particular, in more than one energy spectrum, in particular, two energy spectra. Information that has been acquired during an acquisition for more than one energy spectrum can thus be assigned to an image point in spectrally resolved CT scan data. Monospectral CT scan data, however, is present particularly in only one energy spectrum. Spectrally resolved CT scan data can be present, in particular, in only the region of the scanning field from which CT scan data can be acquired via the first radiation source-detector system and via the second radiation source-detector system for different energy spectra.

The dual-source CT device is therefore configured, in particular, such that it has a first scanning field subregion in which spectrally resolved CT scan data are present and an additional second scanning field subregion in which only monospectral CT scan data are present. Thus, the first scanning field subregion from which, in particular, spectrally resolved CT scan data can be acquired, represents in particular the intersection of the first capture region and the second capture region. In the first scanning field subregion, therefore, the first capture region and the second capture region overlap. If the scanning field set by the user, or automatically, is smaller than the first capture region, then the first scanning field subregion can also constitute only a part of the intersection of the first capture region and the second capture region.

Typically, the first scanning field subregion matches the second capture region of the second radiation source-detector system. The second scanning field subregion from which, in particular, only monospectral CT scan data can be acquired thus represents that part of the scanning region which is located in the first capture region and not in the second capture region. The combination of the first scanning field subregion and of the second scanning field subregion can therefore form the scanning field.

The first CT scan data can thus be acquired both via the first radiation source-detector system and also via the second radiation source-detector system from the first scanning field subregion. The second CT scan data is, in particular, thereby acquired only via the first radiation source-detector system of the dual-source CT device from the second scanning field subregion.

The proposed procedure provides, in particular, that for the reconstruction of the quantitative CT image data from the first scanning field subregion and the second scanning field subregion, different reconstruction methods are used. The results of the two reconstruction processes can then be combined in order to enable a determination of the quantitative material parameter in the entire scanning field.

Herein, the reconstruction of the first quantitative CT image data and the reconstruction of the second quantitative CT image data take place independently of one another. It is also conceivable that in the reconstruction of the second quantitative CT image data, an intermediate result or a result of the reconstruction of the first quantitative CT image data is drawn upon.

The first reconstruction method can herein be tailored to the spectrally resolved first CT scan data present in the first scanning field subregion as input data. Thus, in the first scanning field subregion, the spectrally resolved information can be used as the basis for determining the quantitative material coefficient. In this way, the first quantitative CT image data can be determined with a high degree of accuracy. The second reconstruction method, on the other hand, can be tailored to the monospectral second CT scan data present in the second scanning field subregion as input data. Herein, for the second reconstruction method, only the individual spectrum scan data which has been acquired via the first radiation source-detector system from the second scanning field subregion is available as input data. Using a second reconstruction method specifically suitable for this purpose, the quantitative material coefficient for the second scanning field subregion can now also be reconstructed, possibly with restricted accuracy. In this way, the first quantitative CT image data has, in particular, a higher degree of accuracy in relation to the determination of the quantitative material coefficient than the second CT image data.

The method of at least one embodiment therefore advantageously enables quantitative CT image data to be reconstructed in the entire scanning field of a dual-source CT device operated in dual-energy mode, even if in the outer scanning field subregion of the scanning field due to the different fan-beam arcs of the radiation source-detector systems of the dual-source CT device, only monospectral CT scan data is present. In the second scanning field subregion, herein the second quantitative CT image data can be represented at least approximately. At the same time, in the first scanning field subregion, the first quantitative CT image data reconstructed with great accuracy can be retained.

At least one embodiment of the first reconstruction method which is based upon the spectrally resolved CT scan data as the input data and the second reconstruction method which, in particular, is mainly based upon CT scan data present in a single spectrum can be synergistically utilized in this way. As a synergy effect, the quantitative material coefficient can advantageously be reconstructed for the entire scanning field, wherein in a part of the scanning field, the accuracy of the determination of the quantitative material coefficients can be increased. The combined use of the two reconstruction methods can herein compensate for limitations of the individual methods, so that overall, a better result can be achieved.

One embodiment provides that the first reconstruction method requires spectrally resolved CT scan data as input data and the second reconstruction method accepts monospectral CT scan data as input data.

In this way, the first reconstruction method is particularly advantageously aligned to the first CT scan data as input data, since the first CT scan data is present with two different energy spectra, that is, spectrally resolved. The second reconstruction method, however, is particularly advantageously aligned to the second CT scan data as input data, since it can be acquired solely with the first radiation source-detector system, that is, with one energy spectrum.

One embodiment provides that the first reconstruction method utilizes the presence of the first CT scan data with two different energy spectra in the first scanning field subregion in the reconstruction of the first quantitative CT image data.

The additional information that results from the presence of the first CT scan data with two different energy spectra can be used as known parameters for the determination of the quantitative material parameter. In particular, in the first scanning field subregion, a first CT scan data set which has been acquired via the first radiation source-detector system with a first energy spectrum and a second scan data set which has been acquired via the second radiation source-detector system with a second energy spectrum, are present as input data for the first reconstruction method.

According to a possible procedure of at least one embodiment, initially in the usual manner, for example, by way of a filtered back projection, a first CT image data set is reconstructed from the first CT scan data set and a second CT image data set is reconstructed from the second CT scan data set. The first CT image data set and the second CT image data set can then be processed with one another in order to determine the quantitative material parameters for each image point. One possibility for processing the first CT image data set and the second CT image data set is herein that the CT values in the first CT image data set and in the second CT image data set are considered voxel-wise for each image point. There thus results for each image point a value pair in the basis of the low energy and high energy CT values. This basis can now be transformed by way of a basis transformation to a basis which comprises two quantitative material parameters, for example, electron density and atomic number. In this way, for each image point in the second quantitative CT image data, one or two quantitative material parameters can be determined.

By this, an exact and efficient determination of the first quantitative CT image data is possible for the first scanning field subregion. Naturally, other possibilities are also conceivable for determining the first quantitative CT image data from the spectrally resolved first CT scan data.

One embodiment provides that the second reconstruction method uses the second CT scan data and the portion of the first CT scan data which has been acquired via the first radiation source-detector system, in order to reconstruct the second quantitative CT image data for the whole scanning field exclusively on the basis of the monospectral CT scan data acquired via the first radiation source-detector system from the first scanning field subregion and the second scanning field subregion.

The only input parameter for the second reconstruction method in this case is therefore the monospectral CT scan data acquired via the first radiation source-detector system from the first scanning field subregion and the second scanning field subregion. The second quantitative CT image data is thus determined, in particular, using a part of the first CT scan data and the whole of the second CT scan data. In this way, the second quantitative CT image data can be determined for the entire scanning region. Since the second CT scan data can also be acquired solely via the first radiation source-detector system, according to this procedure, only scan data which has been acquired via the first radiation source-detector system is included in the reconstruction of the second quantitative CT image data.

The input data for reconstruction of the second quantitative CT image data thus lies, in particular, only in a single energy spectrum. A possible second reconstruction method for approximate reconstruction of the quantitative material coefficient exclusively on the basis of monospectral input data is described, for example, in the German patent application DE 10 2015 225 395.3 "Determination of a spatial distribution of a material property value on the basis of a single-energy image recording", the entire contents of which are hereby incorporated herein by reference. The entire content of this patent application and the subsequent application in the United States of America based thereon is hereby incorporated by reference. Naturally, other methods for reconstructing the second quantitative CT image data from monospectral CT scan data are also conceivable.

In this way, it is particularly advantageously possible to reconstruct the second quantitative CT image data for the entire scanning region, that is, also for the second scanning field subregion for which no spectrally resolved CT scan data is present. The determination of the quantitative material parameter can herein take place, in particular, approximately since only monospectral CT scan data is present as input data.

One embodiment provides that the combining of the first quantitative CT image data and the second quantitative CT image data comprises an extraction of the second scanning field subregion from the second quantitative CT image data and the combining of the extracted region with the first quantitative CT image data which images the first scanning field subregion.

In this way, in particular, the image region of the second quantitative CT image data which corresponds to the second scanning field subregion is extracted from the second quantitative CT image data and is added to the first quantitative CT image data. In this way, in particular, values of the quantitative material parameter can be added in an outer region of the scanning field to the first quantitative CT image data. The first quantitative CT image data which can be reconstructed on the basis of the spectrally resolved first CT scan data with a high level of accuracy, remains intact. Thus, only the region of the second quantitative CT image data that has, in particular, a lower accuracy than the first quantitative CT image data is extracted which is not imaged in the first quantitative CT image data. In this way, a particularly advantageous combination of the first quantitative CT image data and the second quantitative CT image data can take place.

One embodiment provides that the second reconstruction method reconstructs from the second CT scan data the second quantitative CT image data for the second scanning field subregion, making use of the spectrally resolved first CT scan data acquired via the first radiation source-detector system and the second radiation source-detector system from the first scanning field subregion.

The second reconstruction method reconstructs, in this case, the second quantitative CT image data exclusively for the second scanning field subregion. The data can then simply be combined with the first quantitative CT image data which covers the first scanning field subregion to the quantitative CT image data. Both the first CT scan data and also the second CT scan data are incorporated as input data into the second reconstruction method. The first CT scan data can herein advantageously comprise information concerning a patient-specific relationship between CT scan data and quantitative CT image data. In this way, particularly advantageously, the spectrally resolved information present in the first scanning field subregion can be used in order to enable the reconstruction of the second quantitative CT image data in the second scanning field subregion.

One embodiment provides that for the reconstruction of the second quantitative CT image data on the basis of the spectrally resolved first CT scan data present in the first scanning field subregion, an imaging function is calculated which enables an allocation of CT scan data to quantitative CT image data, wherein for the second scanning field subregion, the second quantitative CT image data is reconstructed from the second CT scan data making use of the imaging function.

In order to calculate the imaging function, non-quantitative CT image data and the first quantitative CT image data can be reconstructed, for example, from the first CT scan data by way of a filtered back projection. In this way, for example, using point scatter diagrams or regression methods, a relationship can be determined between corresponding image points in the non-quantitative and quantitative CT image data in the first scanning field subregion. In this way, an imaging function which images non-quantitative CT image data onto quantitative CT image data or values of the quantitative material parameter can be determined. For reconstructing the second quantitative CT image data from the second CT scan data, initially non-quantitative CT image data can thus be reconstructed from the second CT scan data and subsequently the imaging function calculated on the basis of the first CT scan data can be applied. In this way, during the reconstruction of the second quantitative CT image data, particularly advantageously, the fact can be used that for the same patients, spectrally resolved CT scan data is present in another scanning field subregion.

One embodiment provides that the second reconstruction method reconstructs from the second CT scan data the second quantitative CT image data for the second scanning field subregion, making use of an imaging function determined with a calibration scan, the imaging function enabling an allocation of CT scan data to quantitative CT image data.

The second reconstruction method reconstructs, in this case, the second quantitative CT image data exclusively for the second scanning field subregion and exclusively on the basis of the monospectral second CT scan data and the imaging function. In this case, the imaging function is, in particular, not specific to the patient from whom the second CT scan data has been acquired. However, the imaging function determined in the calibration scan can be used in a plurality of successive reconstructions, so that the second reconstruction method can effectively determine approximation values for the quantitative material parameter in the second scanning field subregion.

One embodiment provides that during the combination of the first quantitative CT image data and the second quantitative CT image data in a boundary region between the first scanning field subregion and the second scanning field subregion, the first quantitative CT image data and the second quantitative CT image data are included as a weighted combination.

Therefore, in particular, both first quantitative CT image data reconstructed by way of the first reconstruction method and also second quantitative CT image data reconstructed by way of the second reconstruction method are included in a portion of the quantitative CT image data. In the boundary region between the first scanning field subregion and the second scanning field subregion, therefore, a soft transition can be created in the quantitative CT image data. The boundary region can herein have a breadth of several voxels. In this boundary region, values of the quantitative material parameter can be formed by way of a weighted sum from the first quantitative CT image data and the second quantitative CT image data. The weighting factors can herein vary beyond the boundary region, for example, linearly so that a weighting gradient is present in the boundary region.

In this way, it can advantageously be prevented that when combining the first quantitative CT image data and the second quantitative CT image data, a hard recognizable boundary forms between the first quantitative CT image data and the second quantitative CT image data. A soft transition can be created in the quantitative CT image data which improves the image impression of the quantitative CT image data.

One embodiment provides that the quantitative CT image data is provided for the planning of an irradiation of the patient from whom the first CT scan data and the second CT scan data are acquired.

In a radiation therapy, a target volume, for example a tumor, of a patient is irradiated with ionizing radiation. Herein, an external radiation therapy which comprises an irradiation of a body of the patient from outside the body is known. Also known is an internal radiation therapy, also known as brachytherapy. In a brachytherapy, radiation sources which comprise radioactive substances are introduced into a body of the patient in order to damage or destroy the tumor tissue locally in the target volume in the body of the patient. In the planning of the radiation, the quantitative CT image data can be used, in particular, in the case of the electron density or the mass density as quantitative material parameters, for determining the attenuation of the ionizing radiation in the body tissue of the patient. At the same time, a target volume or risk volumes can be determined on the basis of the quantitative CT image data.

In the planning of the irradiation, it is particularly advantageous that the quantitative CT image data is present for the whole scanning field, that is, also in the second scanning field subregion. The reason for this is that for an exact determination of the radiation dose that is fed to the target volume or the risk volume, an attenuation of the radiation in the outer body regions of the patient is also decisive. In this way, the procedure described can then be utilized particularly advantageously if the quantitative CT image data is to be used for the planning of the irradiation of the patient.

At least one embodiment of the inventive solution includes a computation module, the computer unit being configured to carry out at least one embodiment of the inventive method. In this way, the computer unit according to at least one embodiment of the invention can carry out a method for the provision of quantitative CT image data acquired via a dual-source CT device from a scanning field.

For this purpose, in at least one embodiment, the computer unit comprises, in particular, a division unit for division of the scanning field into a first scanning field subregion which represents at least a part of the intersection of the first capture region and the second capture region, and a second scanning field subregion which is disjoint from the second capture region. The computer unit further comprises, in particular, an acquisition unit for the acquisition of first CT data that has been acquired from the first scanning field subregion via the dual-source CT device, and for acquisition of second CT data that has been acquired from the second scanning field subregion via the dual-source CT device. The computer unit also comprises, in particular, a reconstruction unit for reconstructing first quantitative CT image data from the first CT data by way of a first reconstruction method and reconstruction of second quantitative CT image data from the second CT scan data by way of a second reconstruction method which is configured differently from the first reconstruction method. The computer unit comprises, in particular, a combination unit for combining the first quantitative CT image data and the second quantitative CT image data to quantitative CT image data and a provision unit for providing the quantitative CT image data.

The computer unit can thus carry out at least one embodiment of the inventive method independently of the dual-source CT device. For this purpose, the computer unit can, in particular, load the first CT data and the second CT data from a database and/or receive the data from the dual-source CT device directly. The provision of the quantitative CT image data can comprise a transfer of the quantitative CT image data to a display unit and/or a database.

At least one embodiment of the inventive method can thus take place in the form of a post-processing on the computer unit of the CT data acquired by the computer unit. The CT data can be configured as CT scan data, that is in particular, projection data which is received by the dual-source CT device. It is also conceivable that the CT data is configured as already reconstructed non-quantitative CT image data which is received by a reconstruction computer of the dual-source CT device and/or is loaded from a database.

The components of the computer unit, in particular the computation module, can be configured mainly in the form of software components. Fundamentally, these components can also, in part, be realized, in particular if particularly rapid calculations are involved, in the form of software-supported hardware components, for example, FPGAs or the like. Similarly, the required interfaces can be configured, for example, where only an acceptance of data from other software components is concerned, as software interfaces. However, they can also be configured as interfaces constructed from hardware, which are controlled by suitable software. It is naturally also conceivable that a plurality of the aforementioned components are realized in the form of an individual software component or a software-supported hardware component.

The dual-source CT device according to at least one embodiment of the invention comprises a computer unit according to at least one embodiment of the invention.

The computer unit can be configured to transmit control signals to the dual-source CT device and/or to receive and/or process control signals in order to carry out at least one embodiment of an inventive method. The computer unit can be integrated in the dual-source CT device. The computer unit can also be installed separately from the dual-source CT device. The computer unit can be connected to the dual-source CT device.

In this case, the CT data is configured, in particular, as CT scan data. The acquisition of the CT scan data can comprise, in this case, an acquisition of the CT scan data via a capture unit of the dual-source CT device. The CT scan data can then be transferred to the computer unit for further processing. The computer unit can then acquire the CT scan data via the acquisition unit.

The computer program product according to at least one embodiment of the invention is directly loadable into a memory store of a programmable computer unit and has program code segments in order to carry out at least one embodiment of an inventive method when the computer program product is executed in the computer unit. The computer program product can be a computer program or can comprise a computer program. In this way, the method according to at least one embodiment of the invention can be carried out rapidly, exactly reproducibly and robustly.

In at least one embodiment of the invention, the computer program product is configured such that it can carry out the method steps according to at least one embodiment of the invention via the computer unit. The computer unit must have the respective pre-conditions such as, for example, a suitable working memory store, a suitable graphics card or a suitable logic unit so that the respective method steps can be carried out efficiently.

In at least one embodiment of the invention, the computer program product is stored, for example, on a computer-readable medium or is deposited on a network or server from where it can be loaded into the processor of a local computer unit which processor can be directly connected to the dual-source CT device or configured as part of the dual-source CT device.

Furthermore, control information of the computer program product can be stored on an electronically readable data storage medium. The items of control information of the electronically readable data storage medium can be configured such that they carry out at least one embodiment of an inventive method when the data storage medium is used in a computer unit. Thus, the computer program product can also constitute the electronically readable data storage medium.

Examples of electronically readable data storage media are a DVD, a magnetic tape, a hard disk drive or a USB stick, on which electronically readable control information, in particular software (see above) is stored. If this control information (software) is read from the data storage medium and stored in a computer unit of the CT device, all the embodiments according to at least one embodiment of the invention of the above-described methods can be carried out. At least one embodiment of the invention can therefore also proceed from the aforementioned computer-readable medium and/or the aforementioned electronically readable data storage medium.

The advantages of the computer unit according to at least one embodiment of the invention, of the dual-source CT device according to the invention and of the computer program product according to at least one embodiment of the invention substantially correspond to the advantages of the inventive method, as described in detail above. Features, advantages or alternative embodiments mentioned herein are also transferable similarly to the other claimed subject matter and vice versa. In other words, the product claims can also be further developed with the features disclosed or claimed in conjunction with a method. The corresponding functional features of the method are herein configured via suitable product modules as contained herein, in particular, hardware modules.

FIG. 1 shows a dual-source CT device 11 and a computer unit 24 according to an embodiment of the invention. The dual-source CT device is configured for acquiring the CT scan data of a patient 13. The CT scan data can be transferred from the dual-source CT device 11 to the computer unit 24 according to an embodiment of the invention which can acquire the CT image data via an acquisition unit of the computer unit 24 and can subsequently further process it.

The dual-source CT device 11 comprises a gantry 20, a tunnel-shaped opening 9, a patient positioning apparatus 10 and the computer unit 24. The gantry 20 comprises a stationary support frame 21 and a rotor 24. The rotor 24 is arranged rotatable via a rotary mounting apparatus on the stationary support frame 21 about a rotation axis relative to the stationary support frame 21. A patient 13 is introducible into the tunnel-shaped opening 9. In the tunnel-shaped opening 9, a scanning region of the patient 13 is positionable such that an electromagnetic radiation can pass from a radiation source 60A, 63A to the scanning region and following an interaction with the scanning region, can reach a detector element 60B, 63B.

The patient positioning apparatus 10 comprises a positioning table 8 and a transfer panel 12 for positioning the patient 13. The transfer panel 12 is arranged movable relative to the positioning table 8 on the positioning table 8 such that the transfer panel 12 is introducible in a longitudinal direction of the transfer panel 12 into the acquisition region 9.

The dual-source CT device 11 is configured for the acquisition of projection data on the basis of the electromagnetic radiation. Herein, the dual-source CT device 11 comprises a first radiation source-detector system 60 and a second radiation source-detector system 63. The first radiation source-detector system 60 comprises a first radiation source 60A and a group of first detector elements 60B. The second radiation source-detector system 63 comprises a second radiation source 63A and a group of second detector elements 63B. The first radiation source-detector system 60 is operated with a different energy spectrum from that of the second radiation source-detector system 63.

The radiation sources 60A, 60B are arranged on the rotor 24 and are configured for the emission of an X-ray radiation with radiation quanta. The groups of detector elements 63A, 63B are arranged on the rotor 24 and are configured for the detection of the radiation quanta. The radiation quanta can pass from the radiation sources 60A, 60B to the scanning region of the patient 13 and following an interaction with the scanning region, can reach the groups of detector elements 63A, 63B. In this way, projection data, that is CT scan data, of the scanning region is acquired.

The computer unit 24 is configured for receiving the CT scan data acquired from the dual-source CT device 11. The computer unit 24 is configured for controlling the dual-source CT device 11. The computer unit 24 has different computation modules 33, for example, an image reconstruction device. Via the image reconstruction device, for example, on the basis of the CT scan data, quantitative CT image data can be reconstructed.

The dual-source CT device 11 has an input unit and a display unit (both not shown), each of which is connected to the computer unit 24. The input unit is configured for the input of control information, for example, image reconstruction parameters and/or examination parameters. The display unit is configured, in particular, for displaying the quantitative CT image data.

The dual-source CT device 11 disclosed can naturally comprise further components which dual-source CT devices 11 typically have. A general mode of operation of a dual-source CT device 11 is also known to a person skilled in the art, so that a detailed description of the further components is not included.

For the sole execution of at least one embodiment of the inventive method, the computer unit 24 advantageously loads CT scan data from a database via an acquisition unit of the computer unit 24. If the inventive method is carried out by the dual-source CT device 11 and the computer unit 24 in combination, the acquisition unit of the computer unit 24 will acquire, in particular, the CT scan data which has been recorded via the dual-source CT device 11. For this purpose, the computer unit 24 is advantageously connected to the dual-source CT device 11 for a data exchange.

Figure 2:
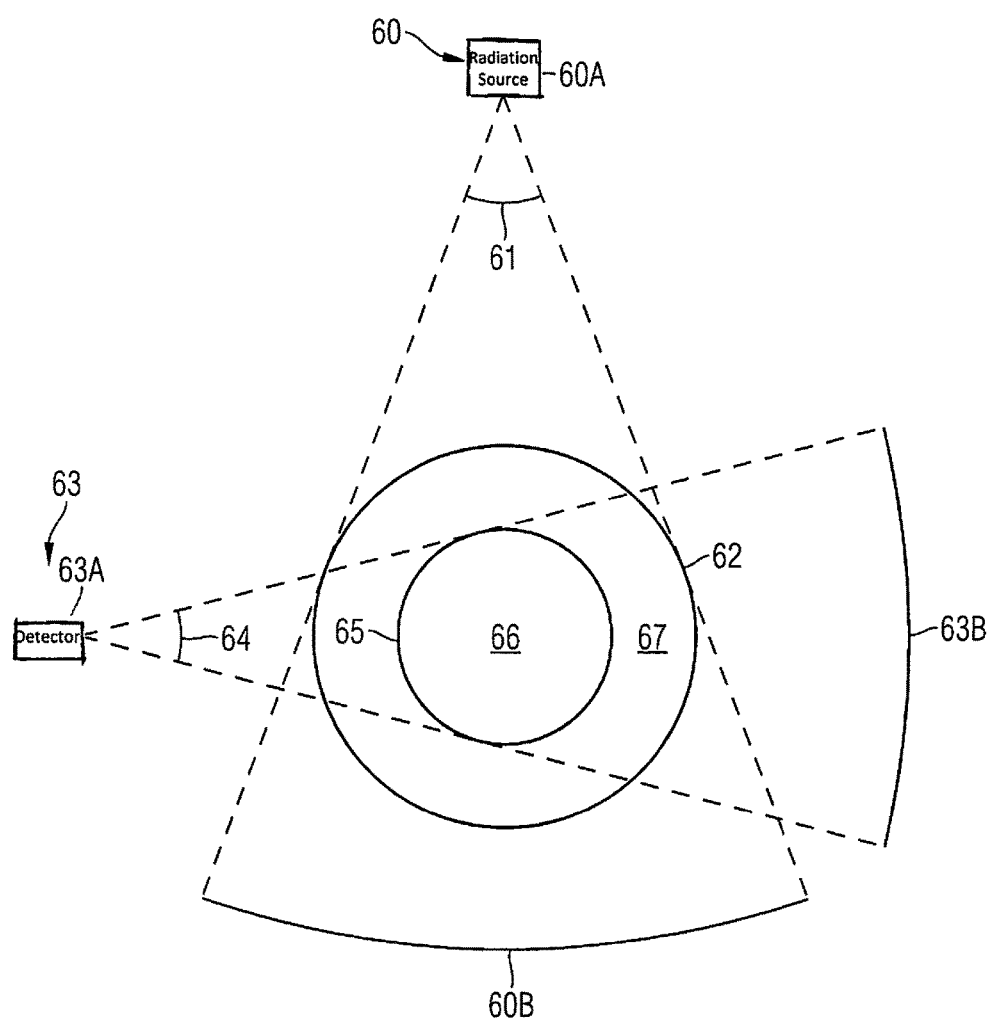
FIG. 2 shows an illustration of the two radiation source-detector systems of the dual-source CT device with their capture regions in a schematic representation.

FIG. 2 shows the two radiation source-detector systems 60, 63 of the dual-source CT device 11 with their capture regions 62, 65 in a schematic representation.

The first radiation source-detector system 60 comprises a first radiation source 60A and a group of first detector elements 60B. The second radiation source-detector system 63 comprises a second radiation source 63A and a group of second detector elements 63B. The first radiation source-detector system 60 is operated with a different energy spectrum from the second radiation source-detector system 63. For example, the first radiation source-detector system 60 is operated with an energy spectrum which has a maximum energy of 140 keV, while the second radiation source-detector system 63 is operated with an energy spectrum which has a maximum energy of 80 keV.

In the case shown in FIG. 2, the first radiation source-detector system 60 has a first fan-beam arc 61 and the second radiation source-detector system 63 has a second fan-beam arc 64, the fan-beam arc 61 being larger than the second fan-beam arc 64. Therefore, for the first radiation source-detector system 60, a first circular capture region 62 in the plane shown in FIG. 2 results. Therefore, for the second radiation source-detector system 63, a second circular capture region 65 in the plane shown in FIG. 2 results. Since the first fan-beam arc 61 is larger than the second fan-beam arc 64, the first circular capture region 62 is also larger than the second circular capture region 65. Thus, in FIG. 2, the case arises that the first capture region 62 and the second capture region 65 are arranged concentrically in one plane, the second capture region 65 in the plane having a smaller radius than the first capture region 62. The second capture region 65 therefore represents a subregion of the first capture region 62. The first capture region 62 can thus, for example, have a diameter of at least 50 cm, whereas the second capture region 65 only has a diameter of not more than 35 cm, for example, 33 cm.

The overall scanning field 66, 67 of the dual-source CT device 11 comprises a first scanning field subregion 66 and a second scanning field subregion 67. The first scanning field subregion 66 is the intersection of the first capture region 62 and the second capture region 65. The second scanning field subregion 66 is that part of the first capture region 62 which is disjoint from the second capture region 65. Therefore, the first scanning field subregion 66 and the second scanning field subregion 67 are also disjoint from one another and together can form the scanning field.

Since CT scan data can be acquired from the first scanning field subregion 66 via both radiation source-detector systems 60, 63 with different energy spectra, in the first scanning field subregion 66, spectrally resolved CT scan data is present. By contrast, from the second scanning field subregion 67, CT scan data can only be acquired via the first radiation source-detector system 60, so that in the second scanning field subregion 67, only monospectral CT scan data is present.

Figure 3:
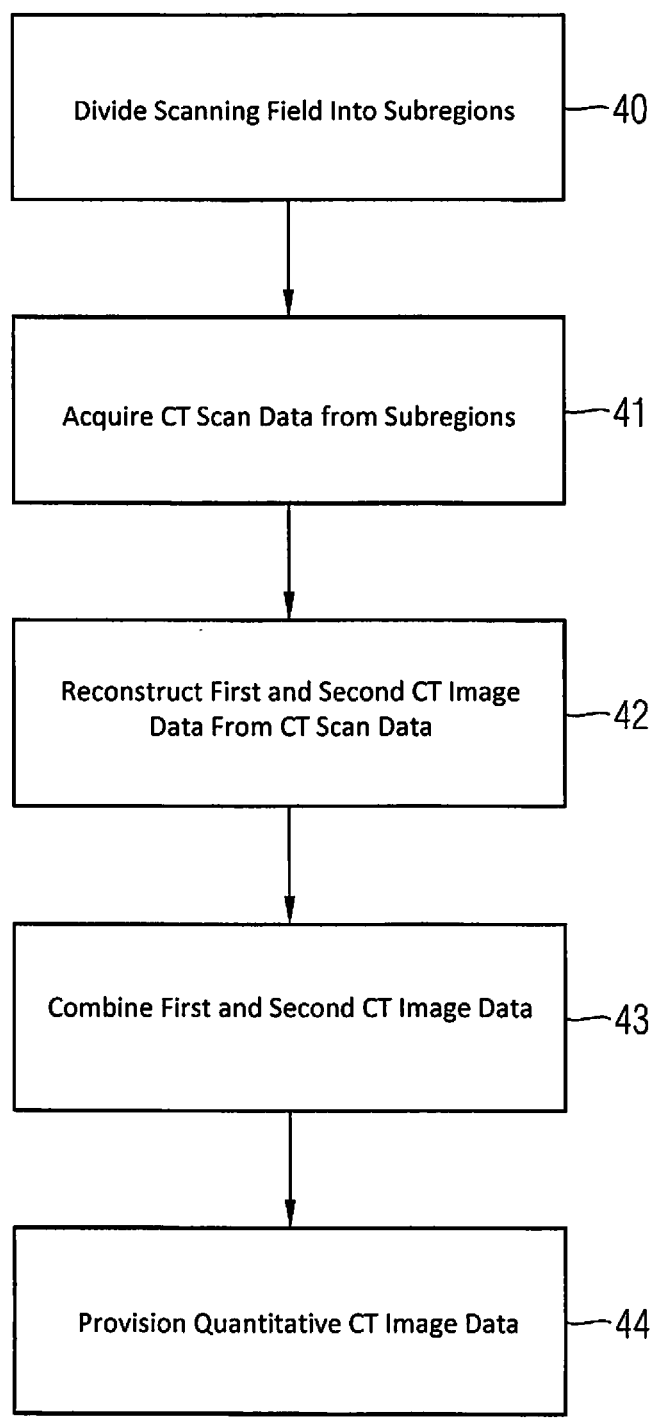
FIG. 3 shows a first embodiment of a method according to an embodiment of the invention.

FIG. 3 shows a flow diagram of a first embodiment of an inventive method for providing quantitative CT image data acquired from a scanning field via a dual-source CT device 11, the dual-source CT device 11 comprising a first radiation source-detector system 60 with a first capture region 62 and a second radiation source-detector system 63 with a second capture region 65, the first radiation source-detector system 60 being operated with a different energy spectrum from that of the second radiation source-detector system 63.

In a first method step 40, a division takes place of the scanning field into a first scanning field subregion 66 which represents at least a part of the intersection of the first capture region 62 and the second capture region 65, and a second scanning field subregion 67 which is disjoint from the second capture region 65.

In a second method step 41, an acquisition takes place of first CT scan data from the first scanning field subregion 66 via the dual-source CT device 11 and acquisition of second CT scan data from the second scanning field subregion 67 via the dual-source CT device 11.

In a further method step 42, a reconstruction takes place of first quantitative CT image data from the first CT scan data by way of a first reconstruction method and reconstruction of second quantitative CT image data from the second CT scan data by way of a second reconstruction method which is configured differently from the first reconstruction method.

In a further method step 43, a combination takes place of the first quantitative CT image data and the second quantitative CT image data to quantitative CT image data.

In a further method step 44, a provision of the quantitative CT image data takes place.

The following description is essentially restricted to the differences from the example embodiment in FIG. 3 wherein, with regard to method steps which remain the same, reference is made to the description of the example embodiment in FIG. 3. Method steps which are substantially the same are, on principle, identified with the same reference signs.

Figure 4:
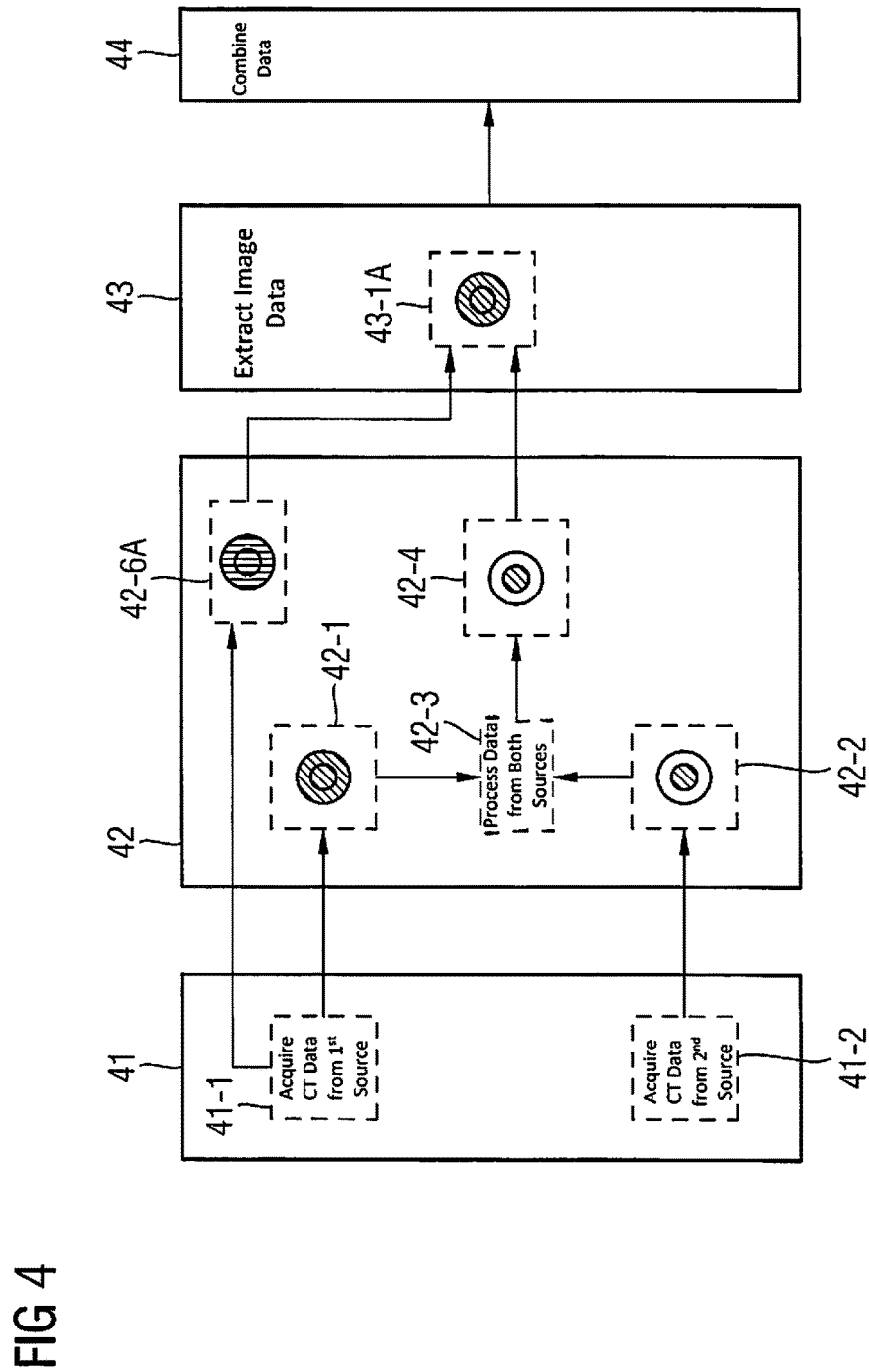
FIG. 4 shows a second embodiment of a method according to an embodiment of the invention.

FIG. 4 shows a flow diagram of a second embodiment of an inventive method.

FIG. 4 shows that in the further method step 41, in a first substep 41-1, CT scan data is acquired via the first radiation source-detector system 60 and, in a second substep 41-2, CT scan data is acquired via the second radiation source-detector system 63. The first CT scan data that is acquired from the first scanning field subregion 66 is thus acquired both in the first substep 41-1 and also in the second substep 41-2. The second CT scan data that is acquired from the second scanning field subregion 67 is thus only acquired in the first substep 41-1 via the first radiation source-detector system 60.

The method step 42-2, the reconstruction of the quantitative CT image data, shows the first reconstruction method and a second possible configuration of the second reconstruction method. In principle, the first reconstruction method requires spectrally resolved CT scan data as input data and the second reconstruction method accepts monospectral CT scan data as input data.

In a first substep 42-1 of the further method step 42, from the CT scan data acquired via the first radiation source-detector system 60, non-quantitative CT image data which images the first capture region 62 is reconstructed by way of a filtered back projection. In a further substep 42-2 of the further method step 42, from the CT scan data acquired via the second radiation source-detector system 63, non-quantitative CT image data which images only the second capture region 65 is reconstructed by way of a filtered back projection. In place of the filtered back projection, naturally other reconstruction methods are also conceivable, for example, algebraic and/or iterative reconstruction methods. The reconstruction of the non-quantitative CT image data can also comprise a pre-processing and/or post-processing for image quality improvement, in particular, for artifact reduction and/or noise reduction. This can, for example, entail a filtration.

The first reconstruction method utilizes, in the further substeps 42-3 and 42-4, the presence of the first CT scan data in the first scanning field subregion 66 with two different energy spectra in the reconstruction of the first quantitative CT image data. For this purpose, in the further substep 42-3, the first scanning field subregion 66 of the non-quantitative CT image data which images the first capture region 62 together with the non-quantitative CT image data which images the second capture region 65 are processed. First quantitative CT image data for the first scanning field subregion 66 result.

In the case shown in FIG. 4, in a further substep 42-6A of the further method step 42, the second reconstruction method uses the second CT scan data and that part of the first CT scan data which has been acquired via the first radiation source-detector system 60, in order to reconstruct the second quantitative CT image data for the whole scanning field exclusively on the basis of the monospectral CT scan data acquired via the first radiation source-detector system 60 in the first substep 41-1 of the further method step 41 from the first scanning field subregion 66 and the second scanning field subregion 67.

Thereafter, the combining of the first quantitative CT image data and the second quantitative CT image data comprises, in the further method step 43, a substep 43-1A in which an extraction of the second scanning field subregion 67 from the second quantitative CT image data takes place, and a combining of the extracted region with the first quantitative CT image data which forms the first scanning field subregion 66.

Figure 5:
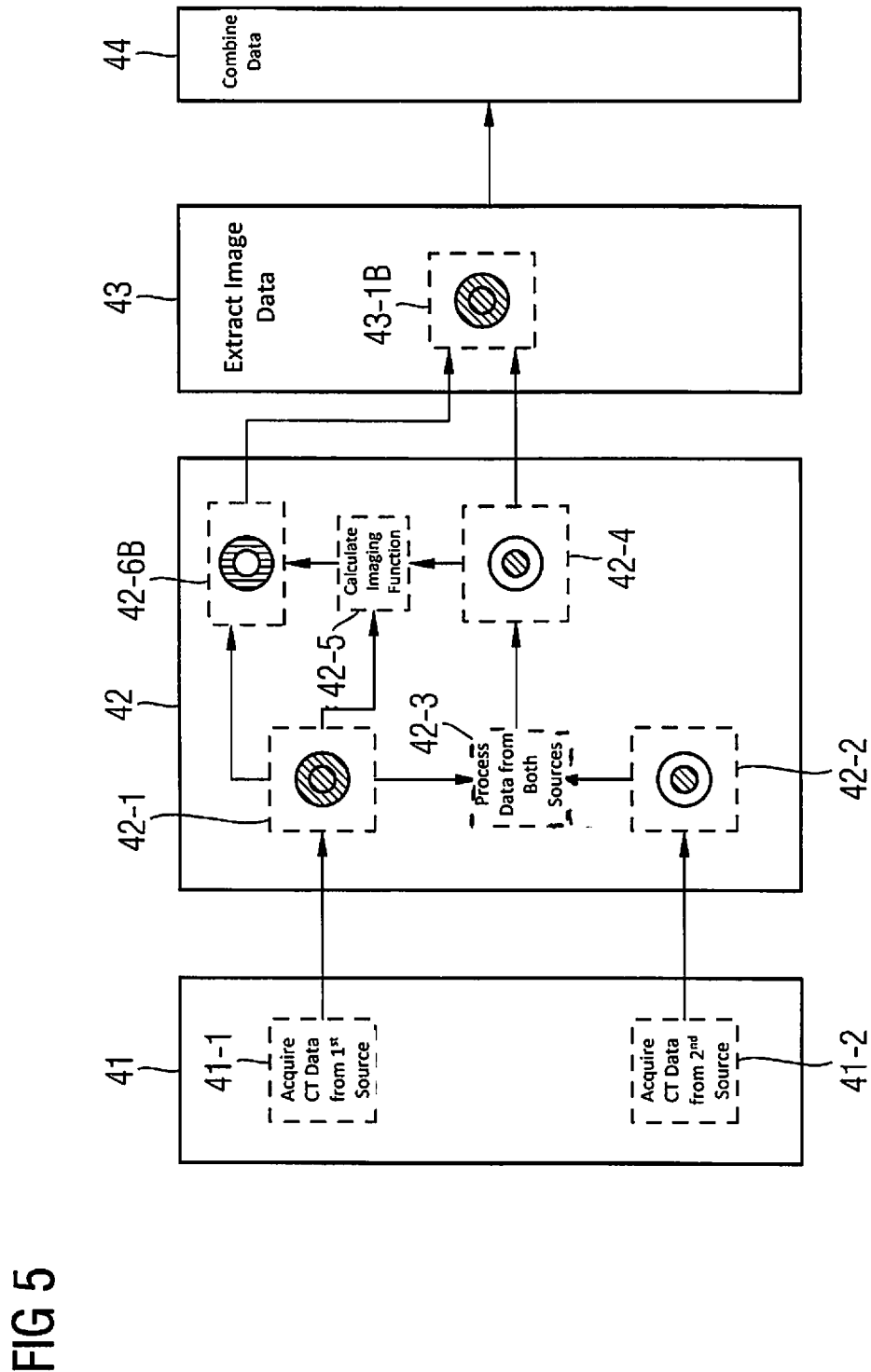
FIG. 5 shows a third embodiment of a method according to an embodiment of the invention.

FIG. 5 shows a flow diagram of a second embodiment of an inventive method.

FIG. 5 substantially differs from FIG. 4 in that in the method step 42-2, a second possible configuration of the second reconstruction method is used. Substeps which remain the same are identified with the same reference signs as in FIG. 4.

The second reconstruction method shown in FIG. 5 reconstructs from the second CT scan data the second quantitative CT image data for the second scanning field subregion 67, making use of the spectrally resolved first CT scan data acquired via the first radiation source-detector system 60 and the second radiation source-detector system 63 from the first scanning field subregion 66. For the reconstruction of the second quantitative CT image data on the basis of the spectrally resolved first CT scan data present in the first scanning field subregion 66, in a further substep 42-5 of the further method step 42, an imaging function is calculated which enables an allocation of CT scan data to quantitative CT image data, wherein for the second scanning field subregion 67, the second quantitative CT image data is reconstructed from the second CT scan data in a further method step 42-6B of the further method step 42, making use of the imaging function.

Therefore initially, as in FIG. 4, the first quantitative CT image data is reconstructed in the further substep 42-4. This first quantitative CT image data is then included as input data in the determination of the imaging function in the further method step 42-5. In the case shown in FIG. 5, the imaging function represents how non-quantitative and quantitative CT image data is associated. The imaging function can then be used to reconstruct, exclusively for the second scanning field subregion 67 in the further substep 42-6B, the second quantitative image data from the non-quantitative image data determined in the first substep 42-1 that is present in the second scanning field subregion 67.

The combining of the first quantitative CT image data and the second quantitative CT image data to quantitative CT image data in the further method step 43 then simply comprises a combination or joining together of the respective CT image data in a substep 43-1B of the further method step 43.

Alternatively to the method shown in FIG. 5, it is also conceivable that the second reconstruction method reconstructs from the second CT scan data the second quantitative CT image data for the second scanning field subregion 67, making use of an imaging function determined with a calibration scan, the imaging function enabling an allocation of CT scan data to quantitative CT image data.

It is also conceivable that during the combination of the first quantitative CT image data and the second quantitative CT image data in a boundary region between the first scanning field subregion 66 and the second scanning field subregion 67, the first quantitative CT image data and the second quantitative CT image data are entered as a weighted combination.

Finally, it is a particularly advantageous field of use that the quantitative CT image data is provided for the planning of an irradiation of the patient 13 from whom the first CT scan data and the second CT scan data are acquired.

The method steps of embodiments of the inventive method shown in FIGS. 3-5 are carried out by the computer unit 24. For this purpose, the computer unit comprises required software and/or computer programs which are stored in a storage unit of the computer unit 24. The software and/or computer programs comprise program segments which are configured to carry out the inventive method when the computer program and/or the software in the computer unit 24 is executed via a processor unit of the computer unit 24.

Although the invention has been illustrated and described in detail based on the preferred example embodiments, the invention is not restricted by the examples given and other variations can be derived therefrom by a person skilled in the art without departing from the protective scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing combined quantitative CT image data acquired from a scanning field via a dual x-ray source CT device, the dual x-ray source CT device including a first x-ray radiation source-detector system with a first capture region and a second x-ray radiation source-detector system with a second capture region, the first x-ray radiation source-detector system being operable with a different energy spectrum than that of the second x-ray radiation source-detector system, the method comprising:
dividing the scanning field into a first scanning field subregion including at least a part of an intersection of the first capture region and the second capture region, and a second scanning field subregion including a portion of the first capture region disjoint from the second capture region;
acquiring first CT scan data from the first scanning field subregion via the dual x-ray source CT device;
acquiring second CT scan data from the second scanning field subregion via the dual x-ray source CT device;

first reconstructing first quantitative CT image data from the first CT scan data by performing a first reconstruction method;
second reconstructing second quantitative CT image data from the second CT scan data by performing a second reconstruction method, the second reconstruction method different from the first reconstruction method;
combining the first quantitative CT image data and the second quantitative CT image data to create combined quantitative CT image data; and
outputting the combined quantitative CT image data.

2. The method of claim 1, wherein
the first CT scan data is spectrally resolved and the first reconstruction method is based on the first CT scan data, and
the second CT scan data is monospectral CT scan data and the second reconstruction method is based on the second CT scan data.

3. The method of claim 2, wherein the first reconstructing includes performing the first reconstruction method based on two different energy spectra in the first CT scan data.

4. The method of claim 3, wherein
the second reconstructing includes performing the second reconstruction method based on the second CT scan data and a portion of the first CT scan data acquired via the first x-ray radiation source-detector system, and
the second reconstructing reconstructs the second quantitative CT image data for the scanning field based on monospectral CT scan data acquired via the first x-ray radiation source-detector system from the first scanning field subregion and the second scanning field subregion.

5. The method as claimed in claim 4, wherein the combining comprises:
extracting third quantitative CT image data corresponding to the second scanning field subregion from the second quantitative CT image data; and
combining the third quantitative CT image data with the first quantitative CT image data.

6. The method of claim 2, wherein the second reconstructing includes performing the second reconstruction method based on the first CT scan data acquired via the first x-ray radiation source-detector system and the second x-ray radiation source-detector system from the first scanning field subregion.

7. The method of claim 6, wherein the second reconstructing further includes:
calculating an imaging function which enables an allocation of CT scan data to quantitative CT image data; and
reconstructing the second quantitative CT image data based on the imaging function.

8. The method of claim 2, wherein the second reconstructing includes performing the second reconstruction method based on an imaging function determined based on a calibration scan, the imaging function enabling an allocation of CT scan data to quantitative CT image data.

9. A non-transitory computer readable medium, storing program code segments that, when executed by at least one processor, causes the at least one processor to perform the method of claim 2.

10. The method of claim 1, wherein the first reconstructing includes performing the first reconstruction method based on two different energy spectra in the first CT scan data.

11. The method of claim 10, wherein
the second reconstructing includes performing the second reconstruction method based on the second CT scan data and a portion of the first CT scan data acquired via the first x-ray radiation source-detector system, and
the second reconstructing reconstructs the second quantitative CT image data for the scanning field based on monospectral CT scan data acquired via the first x-ray radiation source-detector system from the first scanning field subregion and the second scanning field subregion.

12. The method as claimed in claim 11, wherein the combining comprises:
extracting third quantitative CT image data corresponding to the second scanning field subregion from the second quantitative CT image data; and
combining the third quantitative CT image data with the first quantitative CT image data.

13. The method of claim 10, wherein the second reconstructing includes performing the second reconstruction method based on the first CT scan data acquired via the first x-ray radiation source-detector system and the second x-ray radiation source-detector system from the first scanning field subregion, the first CT scan data being spectrally resolved.

14. The method of claim 13, wherein the second reconstructing further includes:
calculating an imaging function which enables an allocation of CT scan data to quantitative CT image data; and
reconstructing the second quantitative CT image data based on the imaging function.

15. The method of claim 10, wherein the second reconstructing includes performing the second reconstruction method based on an imaging function determined based on a calibration scan, the imaging function enabling an allocation of CT scan data to quantitative CT image data.

16. The method of claim 1, wherein
the second reconstructing includes performing the second reconstruction method based on the second CT scan data and a portion of the first CT scan data acquired via the first x-ray radiation source-detector system, and
the second reconstructing reconstructs the second quantitative CT image data for the scanning field based on monospectral CT scan data acquired via the first x-ray radiation source-detector system from the first scanning field subregion and the second scanning field subregion.

17. The method as claimed in claim 16, wherein the combining comprises:
extracting third quantitative CT image data corresponding to the second scanning field subregion from the second quantitative CT image data; and
combining the third quantitative CT image data with the first quantitative CT image data.

18. The method of claim 1, wherein the second reconstructing includes performing the second reconstruction method based on the first CT scan data acquired via the first x-ray radiation source-detector system and the second x-ray radiation source-detector system from the first scanning field subregion, the first CT scan data being spectrally resolved.

19. The method of claim 18, wherein the second reconstructing further includes:
calculating an imaging function which enables an allocation of CT scan data to quantitative CT image data; and
reconstructing the second quantitative CT image data based on the imaging function.

20. The method of claim 1, wherein the second reconstructing includes performing the second reconstruction method based on an imaging function determined based on a calibration scan, the imaging function enabling an allocation of CT scan data to quantitative CT image data.

21. The method of claim 1, wherein the combined quantitative CT image data includes a boundary region between the first scanning field subregion and the second scanning field subregion in which the first quantitative CT image data and the second quantitative CT image data are combined as a weighted combination.

22. The method of claim 1, further comprising:
planning an x-ray irradiation of a patient based on the combined quantitative CT image data.

23. A non-transitory computer readable medium, storing program code segments that, when executed by at least one processor, causes the at least one processor to perform the method of claim 1.

24. A dual x-ray source CT device comprising:
at least one processor; and
the non-transitory computer readable medium of claim 23.

25. A computer unit comprising:
a memory storing computer-readable instructions; and
at least one processor, configured to execute the computer-readable instructions to perform a method for providing combined quantitative CT image data acquired from a scanning field via a dual x-ray source CT device, the dual x-ray source CT device including a first x-ray radiation source-detector system with a first capture region and a second x-ray radiation source-detector system with a second capture region, the first x-ray radiation source-detector system being operable with a different energy spectrum from the second x-ray radiation source-detector system, the method including,
dividing the scanning field into a first scanning field subregion including at least a part of an intersection of the first capture region and the second capture region, and a second scanning field subregion including a portion of the first capture region disjoint from the second capture region,
acquiring first CT scan data from the first scanning field subregion via the dual x-ray source CT device,
acquiring second CT scan data from the second scanning field subregion via the dual x-ray source CT device,
first reconstructing first quantitative CT image data from the first CT scan data by performing a first reconstruction method,
second reconstructing second quantitative CT image data from the second CT scan data by performing a second reconstruction method, the second reconstruction method differently from the first reconstruction method,
combining the first quantitative CT image data and the second quantitative CT image data to create combined quantitative CT image data, and
outputting the combined quantitative CT image data.

26. A dual x-ray source CT device comprising the computer unit of claim 25.

* * * * *